(12) United States Patent
Schehlmann et al.

(10) Patent No.: US 6,482,393 B1
(45) Date of Patent: Nov. 19, 2002

(54) HAIRSETTING COMPOSITIONS

(75) Inventors: Volker Schehlmann, Mannheim; Karin Sperling-Vietmeier, Neustadt; Axel Sanner, Frankenthal; Rainer Blankenburg, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/537,908

(22) PCT Filed: Apr. 19, 1994

(86) PCT No.: PCT/EP94/01205

§ 371 (c)(1),
(2), (4) Date: Oct. 26, 1995

(87) PCT Pub. No.: WO94/24986

PCT Pub. Date: Nov. 10, 1994

(30) Foreign Application Priority Data

Apr. 30, 1993 (DE) .......................................... 43 14 305

(51) Int. Cl.$^7$ ................................................. A61K 7/11
(52) U.S. Cl. .................. 424/47; 424/70.16; 526/318.44
(58) Field of Search ................................. 424/47, 70.16; 526/318.44

(56) References Cited

U.S. PATENT DOCUMENTS

| | | | |
|---|---|---|---|
| 3,927,199 A | * 12/1975 | Micchelli et al. ............. | 424/47 |
| 4,192,861 A | 3/1980 | Michelli et al. ............... | 424/47 |
| 4,842,852 A | * 6/1989 | Nowak, Jr. et al. ........... | 424/71 |
| 4,874,604 A | 10/1989 | Sramek ....................... | 424/47 |
| 5,132,417 A | 7/1992 | Potthoff-Karl ............... | 526/264 |
| RE34,157 E | * 1/1993 | Sramek ....................... | 424/47 |
| 5,196,188 A | 3/1993 | Potthoff-Karl ............... | 424/71 |
| 5,306,484 A | * 4/1994 | Potthoff-Karl et al. ........ | 424/47 |

* cited by examiner

Primary Examiner—Margaret G. Moore
(74) Attorney, Agent, or Firm—Keil & Weinkauf

(57) ABSTRACT

Hairsetting compositions comprise as film-formers copolymers based on tert-butyl acrylate or tert-butyl methacrylate having a K value of from 10 to 50 which are obtainable by free-radical polymerization of A) from 30 to 72% by weight of tert-butyl acrylate or tert-butyl methacrylate or a mixture thereof as monomer A, B) from 10 to 28% by weight of acrylic acid or methacrylic acid or a mixture thereof as monomer B, and C) from 0 to 60% by weight of a free-radically copolymerizable monomer or of a free-radically copolymerizable monomer mixture as monomers C, where at least one of the monomers C produces a homopolymer having a glass transition temperature of less than 30° C., the carboxyl groups of the copolymers being partially or completely neutralized.

3 Claims, No Drawings

HAIRSETTING COMPOSITIONS

The present invention relates to novel hairsetting compositions which comprise as film-formers copolymers based on tert-butyl acrylate or tert-butyl methacrylate having a K value of from 10 to 50 and which are obtainable by free-radical polymerization of A) from 30 to 72% by weight of tert-butyl acrylate or tert-butyl methacrylate or a mixture thereof as monomer A, B) from 10 to 28% by weight of acrylic acid or methacrylic acid or a mixture thereof as monomer B, and C) from 0 to 60% by weight of a free-radically copolymerizable monomer or of a free-radically copolymerizable monomer mixture as monomers C, where at least one of the monomers C produces a homopolymer having a glass transition temperature of less than 30° C., the carboxyl groups of the copolymers being partially or completely neutralized.

EP-A 379 082 discloses hairsetting compositions which comprise as film-formers copolymers based on tert-butyl acrylate and/or tert-butyl methacrylate having a K value of from 10 to 50, which are obtainable by free-radical polymerization of A) from 75 to 99% by weight of tert-butyl acrylate and/or tert-butyl methacrylate, B) from 1 to 25% by weight of acrylic acid and/or methacrylic acid, and C) from 0 to 10% by weight of a further free-radically copolymerizable monomer, the carboxyl groups of the copolymers being, as usual, partially or completely neutralized by amines.

Parameters of these prior-art compositions which are still in need of improvement, however, are the ease of washoff of the polymer from the hair, the solubility of the film-former in aqueous formulations, which are nowadays increasingly displacing those formulations based solely on organic solvents which are ecologically acceptable, and the handle and set of the treated hair, since hair which is treated with the prior-art hairsetting compositions generally feels too brittle or too coarse.

It is an object of the present invention to prepare a hairsetting composition which no longer has the abovementioned disadvantages.

We have found that this object is achieved by the hairsetting compositions defined at the outset.

The monomer or monomers C serve to modify the properties of the copolymer. In a preferred embodiment, monomers used are $C_1$–$C_{18}$-alkyl acrylates or methacrylates, especially $C_1$–$C_4$-alkyl acrylates or methacrylates, or a mixture of these (meth)acrylates with N-$C_1$–$C_{18}$-alkylacrylamides or -methacrylamides, especially N—$C_1$–$C_4$-alkylacrylamides or -methacrylamides. In these (meth)-acrylates and (meth)acrylamides, $C_1$–$C_4$-alkyl is suitably methyl, ethyl, n-propyl, isopropyl, n-butyl, isobutyl, sec-butyl or tert-butyl.

Particularly good results are obtained when C comprises un-branched $C_2$–$C_4$-alkyl acrylates, alone or as a mixture with branched N—$C_3$–$C_4$-alkylacrylamides. Particular preference is given to the use for this purpose of ethyl acrylate or of a mixture of ethyl acrylate and N-tert-butylacrylamide.

In a preferred embodiment, the composition of the copolymer used as film-former is A) from 50 to 72% by weight, in particular from 60 to 70% by weight, of monomer A, B) from 12 to 25% by weight, in particular from 15 to 23% by weight, of monomer B, and C) from 3 to 38% by weight, in particular from 7 to 25% by weight, of monomer C.

The upper limit of 72% by weight for monomer A is particularly critical since above this limit the advantageous properties of the hairsetting composition of the invention are no longer found. The marked change in the spectrum of properties of the hairsetting composition between a content of 72 and 75% by weight of monomer A was surprising in particular in the context of the compositions from EP-A 379 082.

In a further preferred embodiment, the copolymer used as film-former is composed of A) tert-butyl acrylate as monomer A, B) methacrylic acid as monomer B, and C) ethyl acrylate or a mixture of ethyl acrylate and N-tert-butylacrylamide as monomer C.

The copolymers described are prepared in a known manner by free-radical copolymerization of the monomers A, B and, if used, C. The reaction is carried out by the usual polymerization techniques, for example by the methods of suspension, emulsion or solution polymerization.

The polymerization reaction, which proceeds by a free-radical mechanism, is initiated by the customary peroxo or azo compounds, for example dibenzoyl peroxide, tert-butyl perpivalate, tert-butyl per-2-ethylhexanoate, di-tert-butyl peroxide, tert-butyl hydroperoxide, 2,5-dimethyl-2,5-di(tert-butylperoxy)hexane, alkali metal persulfates or ammonium persulfates, azobisisobutyronitrile, hydrogen peroxide or redox initiators, advantageously in amounts of from 0.1 to 2% by weight, based on the weight of the monomers. The amounts of monomers and solvents or dispersants are advantageously chosen so as to give from 30 to 80% strength by weight solutions or dispersions, or suspensions, of the copolymers. The content of residual monomer can be reduced by postpolymerization in accordance with generally known methods.

The copolymers have K values of from 10 to 60, preferably from 15 to 40. The particular K value desired can be established in a manner known per se by appropriate choice of the polymerization conditions, such as the temperature of polymerization and the concentration of initiator. If desired, especially when employing emulsion and suspension polymerization, it may be appropriate to use regulators, especially sulfur compounds such as mercaptoethanol, 2-ethylhexyl thioglycolate, thioglycolic acid or dodecylmercaptan, in order to reduce the K value. The K values are measured in accordance with Fikentscher, Cellulosechemie, Vol. 13 (1932) 58 to 64 at 25° C. in 1% strength by weight ethanolic solution and are a measure of the molecular weight.

Such copolymers normally have glass transition temperatures of between 50 and 130° C., in particular between 60 and 100° C.

When the hairsetting composition is prepared by emulsion polymerization the resulting dispersion can be either incorporated directly into an aqueous hairsetting formulation or dried, for example by spraydrying, so that the hairsetting composition can be processed and used in powder form.

For use in the hairsetting compositions of the invention, the carboxyl groups of the copolymers thus obtained are usually neutralized with an alkali metal hydroxide or, preferably, with an amine, partially or completely, advantageously to the extent of from 5 to 100%, preferably from 30 to 95%. Neutralization is preferably carried out with a mono-, di- or trialkanolamine having 2 to 5 carbon atoms in the alkanol radical, which may be in etherified form, for example mono-, di- and triethanolamine, mono-, di- and tri-n-propanolamine, mono-, di- and triisopropanolamine, 2-amino-2-methylpropanol and di(2-methoxyethyl)amine, an alkanediolamine having 2 to 5 carbon atoms, for example 2-amino-2-methyl-1,3-propanediol and 2-amino-2-ethyl-1,3-propanediol, or a primary, secondary or tertiary alkylamine having a total of 5 to 10 carbon atoms, for example N,N-diethylpropylamine.

Particularly good results are obtained with 2-amino-2-methylpropanol, triisopropanolamine and 2-amino-2-ethyl-1,3-propanediol.

Particularly suitable alkali metal hydroxides for the neutralization are sodium hydroxide and potassium hydroxide.

The hairsetting compositions according to the invention are employed, for example, as gels, lotions, mousses and, in particular, as hairsprays. Particularly preferred hairspray formulations are those comprising the following constituents:

from 0.1 to 20% by weight, preferably from 0.5 to 10% by weight, in particular from 2 to 10% by weight, of the partially or completely neutralized copolymer from 1 to 99.9% by weight, preferably from 5 to 50% by weight, in particular from 10 to 40% by weight, of water from 0 to 95% by weight, preferably from 20 to 60% by weight, in particular from 25 to 50% by weight, of a customary organic solvent such as, in particular, ethanol, isopropanol or dimethoxymethane, or else acetone, n-propanol, n-butanol, 2-methoxy-1-propanol, n-pentane, n-hexane, cyclohexane, n-heptane, n-octane or dichloromethane, or a mixture thereof from 0 to 90% by weight, preferably from 30 to 80% by weight, in particular from 45 to 70% by weight, of a customary propellant such as propane, n-butane, isobutane, 2,2-dimethylbutane, n-pentane, isopentane, dimethyl ether, difluoroethane, fluorotrichloromethane, dichlorodifluoromethane or dichlorotetrafluoroethane, or a mixture thereof.

Compounds from the above especially employed as propellants are the hydrocarbons, especially propane, n-butane, n-pentane and mixtures thereof, and also dimethyl ether and difluoroethane. If desired, one or more of the abovementioned chlorinated hydrocarbons can be used as a component of propellant mixtures, but only in a minor proportion, for instance up to 20% by weight based on the propellant mixture.

The hairsetting compositions according to the invention are also particularly suitable for pump spray formulations without the addition of propellants, and for aerosol sprays with customary pressurized gases, such as nitrogen, compressed air or carbon dioxide as propellants.

These spray formulations may additionally contain minor amounts of perfume oils, for example from 0.1 to 0.5% by weight.

A standard aqueous spray formulation has, for example, the following composition:

from 2 to 10% by weight of the copolymer 100% neutralized with 2-amino-2-methylpropanol from 10 to 76% by weight of ethanol from 2 to 40% by weight of water from 10 to 40% by weight of dimethyl ether The copolymers present in the novel hairsetting compositions are notable for their high degree of compatibility with the apolar propellants in spray formulations, especially with hydrocarbons such as propane, n-butane or mixtures thereof. They give a good hairsetting effect, which is evident from the high values for curl retention which are usually above 80% in this context. The compositions are also notable for causing almost no sticking of the hair.

However, it is in those applications-related properties which were designated as being in need of improvement, when discussing the prior-art compositions at the outset, that the novel hairsetting compositions show particularly outstanding results. In alcohols such as ethanol or isopropanol and in mixtures of these alcohols with water, they give clear solutions. The clarity of the solutions is retained even if the solutions are employed in standard spray formulations together with propellants such as dimethyl ether. The novel hairsetting compositions can be washed out of the hair very readily. Hair treated with them is of heightened sleekness and has a pleasant natural handle. At the same time, the setting effect achieved is high, so that it is possible in principle to reduce the requisite amount of film-former in the hairspray formulation.

In order to tailor the properties of hairsetting compositions it can be advantageous to employ the copolymers of the invention as a mixture with other hairsetting polymers. Further suitable hairsetting polymers are commercially available polymers such as polyvinylpyrrolidones, copolymers of vinylpyrrolidone and vinyl acetate, copolymers of vinyl acetate and crotonic acid, copolymers of vinyl acetate, vinyl propionate and crotonic acid or copolymers based on acrylate/acrylamide. Such mixtures can contain the copolymers of the invention and the other hairsetting polymers in a weight ratio of from 1:99 to 99:1.

EXAMPLES

Preparation instructions for Examples 1 to 15 and Comparison Examples A to D

Example 2 (Emulsion Polymerization)

1 g of sodium lauryl sulfate, 6.7 g of a commercial nonionic emulsifier, 100 g of water, 1.3 g of ethylhexyl thioglycolate, 60 g of methacrylic acid, 210 g of tert-butyl acrylate and 30 g of ethyl acrylate were used to prepare an emulsion which was metered at from about 75 to 85° C. over the course of from about 2 to 4 hours, in the course of the polymerization, into a polymerization vessel containing 500 g of water. The initiator, a solution of 1 g of sodium persulfate in 100 g of water, was likewise run in continuously during the polymerization. In order to reduce the content of residual monomer, a redox initiator (tert-butyl hydroperoxide/ascorbic acid) was subsequently added and the mixture subjected to postpolymerization.

The preparation of Examples 1, 3 to 11 and A to D was analogous to that of Example 2.

Example 12 (Solution Polymerization)

A mixture of 105 g of tert-butyl acrylate, 30 g of ethyl acrylate, 15 g of acrylic acid, 0.5 g of tert-butyl perpivalate and 25 g of ethanol was heated to 75° C. After the commencement of polymerization, which was evident from an increase in viscosity, a mixture of 945 g of tert-butyl acrylate, 270 g of ethyl acrylate, 135 g of acrylic acid and 270 g of ethanol, and a solution of 6.0 g of tert-butyl perpivalate in 90 g of ethanol, were added simultaneously over the course of 6 hours, the mixture being maintained at a gentle boil at from 77 to 80° C. A solution of 3.0 g of 2,5-dimethyl-2,5-di(tert-butylperoxy)hexane in 400 g of ethanol was then added, after which the reaction vessel was sealed pressure-tight, heated to 130° C. and maintained at this temperature for 3 hours. The polymer content of the resulting solution was adjusted to 50% by weight with about 550 g of ethanol. The terpolymer had a K value of 32.5 (measured in 1.0% strength ethanolic solution at 25° C.).

The preparation of Examples 13 and 14 was analogous to that of Example 12.

Example 15 (Suspension Polymerization)

70 g of tert-butyl acrylate, 12 g of ethyl acrylate and 18 g of methacrylic acid were heated in succession to 70° C. with stirring in 250 g of water containing 0.9 g of polyacrylic acid of molecular weight 250,000, 1 g of a commercial emulsifier based on a paraffinsulfonate mixture having an average chain length of 14 to 15 carbon atoms and 0.3 g of 2-mercaptoethanol as regulator. 0.02 g of tert-butyl per-2-ethylhexanoate was then added in small portions. After the final portion of initiator had been added, polymerization was continued to completion at 90° C. for 3.5 hours more. Steam was then passed through at 100° C. until about 300 g of water had distilled over in the course of 4 hours, with complete removal of residual monomer. The resulting polymer suspension was filtered, washed with water to remove very fine undissolved particles, and dried in a stream of air at about 50° C. to give a flowable powder having average particle sizes of from 0.3 to 1.5 mm. The K value was 40 (measured 1% strength by weight solution in ethanol).

Application Properties

The table below gives the figures for the composition, curl retention, ease of washoff, solubility, handle and setting effect of Examples 1 to 15 and of Comparison Examples A to D.

The curl retention is a measure of the hairsetting effect under extreme climatic conditions. It is measured in a model test on locks of hair treated by producing a customary water-wave on hair about 15 cm long and sprayed with the respective spray formulation from a distance of 10 cm for 4 seconds. After the locks had spent 5 hours suspended in a climate-controlled chamber at 25° C. and 90% relative atmospheric humidity, the relative deformation (extension) of the locks, based on their original shape, is determined. A high value denotes a high setting effect, ie. at 100% the original shape was retained completely.

The ease of washoff of the polymer from the hair, the handle (the feel of the treated hair) and the setting effect (the strength of the setting of hair on a headform) were each rated on a scale of 1 to 5, where 1=very good 2=good 3=still acceptable 4=poor 5=very poor The solubility of the polymer to give a clear solution was assessed in a mixture of ethanol, water and polymer in a weight ratio of 55:40:5, as follows:

+=clear solution−=cloudy

All measurements and ratings were determined using a customary, standard spray formulation in which the copolymer was 100% neutralized with 2-amino-2-methylpropanol.

Key to table

| TBA | = tert-butyl acrylate |
| MAA | = methacrylic acid |
| AA | = acrylic acid |
| EA | = ethyl acrylate |
| TBAA | = N-tert-butylacrylamide |

TABLE

Composition and applicational properties of Examples 1 to 11 and of Comparison Examples A to D

| Ex. No. | Composition [% by weight] | | | | | Curl retention [%] | Ease of washoff [rating] | Solubility [+/−] | Handle [rating] | Setting effect [rating] |
|---|---|---|---|---|---|---|---|---|---|---|
| | TBA | MAA | AA | EA | TBAA | | | | | |
| 1 | 72 | 18 | — | 10 | — | 84 | 2 | + | 2 | 2 |
| 2 | 70 | 20 | — | 10 | — | 88 | 2 | + | 1 | 1 |
| 3 | 60 | 20 | — | 20 | — | 84 | 1 | + | 1 | 1 |
| 4 | 58 | 22 | — | 20 | — | 73 | 1 | + | 2 | 2 |
| 5 | 50 | 20 | — | 20 | 10 | 88 | 2 | + | 2 | 2 |
| 6 | 60 | 20 | — | 10 | 10 | 79 | 2 | + | 1 | 1 |
| 7 | 40 | 25 | — | 25 | 10 | 76 | 1 | + | 2 | 2 |
| 8 | 65 | 20 | — | 5 | 10 | 80 | 1 | + | 1 | 1 |
| 9 | 65 | 15 | — | 10 | 10 | 82 | 2 | + | 1 | 1 |
| 10 | 35 | 20 | — | 20 | 25 | 66 | 1 | + | 1 | 1 |
| 11 | 40 | 20 | — | 20 | 20 | 75 | 1 | + | 1 | 1 |
| 12 | 70 | — | 10 | 20 | — | 79 | 2 | + | 1 | 1 |
| 13 | 65 | 15 | — | 20 | — | 77 | 3 | + | 1 | 2 |
| 14 | 70 | 20 | — | 10 | — | 89 | 1 | + | 1 | 1 |
| 15 | 70 | 18 | — | 12 | — | 84 | 2 | + | 1 | 1 |

| Ex. | Composition [% by weight] | | | | | Curl retention [%] | Ease of washoff [rating] | Solubility [+/-] | Handle [rating] | Setting effect [rating] |
|---|---|---|---|---|---|---|---|---|---|---|
| No. | TBA | MAA | AA | EA | TBAA | | | | | |
| for comparison: | | | | | | | | | | |
| A | 85 | 15 | — | — | — | 89 | 4 | − | 5 | 5 |
| B | 75 | 25 | — | — | — | 85 | 1 | + | 5 | 5 |
| C | 75 | 15 | — | 10 | — | 86 | 4 | − | 3 | 3 |
| D | 75 | 20 | — | 5 | — | 84 | 2 | + | 3 | 3 |

We claim:

1. A hair setting composition comprising as film-formers copolymers consisting essentially of tert-butyl acrylate or tert-butyl methacrylate having a K value of from 10 to 50 which are obtained by free-radical polymerization of monomers consisting of
   A) from 50 to 72% by weight, based on the total weight of monomers employed in the polymerization, of tert-butyl acrylate or tert-butyl methacrylate or a mixture thereof as monomer A,
   B) from 12 to 25% by weight, based on the total weight of monomers employed in the polymerization, of acrylic acid or methacrylic acid or a mixture thereof as monomer B, and
   C) from 3 to 38% by weight, based on the total weight of monomers employed in the polymerization, of a free-radically copolymerizable monomer capable of forming a homopolymer having a glass transition temperature of less than 30° C., which monomer is ethyl acrylate, wherein any carboxyl groups present in the copolymer are partially or completely neutralized.

2. A hairsetting composition in the form of a spray formulation comprising, in addition to solvents for such formulations and, optionally, propellants, from 0.1 to 20% by weight of a copolymer as in claim 1.

3. A hairsetting composition as claimed in claim 1, additionally comprising other polymers which are suitable for setting hair.

* * * * *

Disclaimer

6,482,393 B1 — Schehlmann et al. Mannheim (DE). HAIRSETTING COMPOSITIONS. Patent dated Nov. 19, 2002, Disclaimer filed Apr. 15, 2005, by the Assignee, BASF Aktiengesellschaft.

This patent is subject to a terminal disclaimer.

*(Official Gazette June 14, 2005)*